United States Patent [19]

Yeung et al.

[11] Patent Number: 4,498,774
[45] Date of Patent: Feb. 12, 1985

[54] MICRO-POLARIMETER FOR HIGH PERFORMANCE LIQUID CHROMATOGRAPHY

[75] Inventors: Edward E. Yeung, Ames, Iowa; Larry E. Steenhoek, Wilmington, Del.; Steven D. Woodruff, Morgantown, W. Va.; Jeng-Chung Kuo, Skokie, Ill.

[73] Assignee: Iowa State University Research Foundation, Inc., Ames, Iowa

[21] Appl. No.: 489,031

[22] Filed: Apr. 27, 1983

Related U.S. Application Data

[63] Continuation-in-part of Ser. No. 286,026, Jul. 22, 1981, abandoned.

[51] Int. Cl.[3] .................... G01N 21/21; G01N 31/06
[52] U.S. Cl. ................................. 356/368; 356/410; 356/411; 422/70; 436/161
[58] Field of Search ............... 356/364, 365, 368, 410, 356/411; 422/70; 436/161

[56] References Cited

U.S. PATENT DOCUMENTS 3,602,597  8/1971  Sproul ............................. 356/365
3,738,755  6/1973  Chaney et al. ..................... 356/368

OTHER PUBLICATIONS

Yeung et al., A New HPLC Detector Based on Optical Activity, Pitt. Conf., Analytical Chem. and Appl. Spectroscopy, Abstract 580, 3-13-80.
Scaparo et al., Appl. Phys. Lett., 35(7), Oct. 1, 1979.

Primary Examiner—Michael S. Marcus
Attorney, Agent, or Firm—Zarley, McKee, Thomte, Voorhees & Sease

[57] ABSTRACT

A micro-polarimeter interfaced with a system for high performance liquid chromatography, for quantitatively analyzing micro and trace amounts of optically active organic molecules, particularly carbohydrates. A flow cell with a narrow bore is connected to a high performance liquid chromatography system. Thin, low birefringence cell windows cover opposite ends of the bore. A focused and polarized laser beam is directed along the longitudinal axis of the bore as an eluent containing the organic molecules is pumped through the cell. The beam is modulated by air gap Faraday rotators for phase sensitive detection to enhance the signal to noise ratio. An analyzer records the beams's direction of polarization after it passes through the cell. Calibration of the liquid chromatography system allows determination of the quantity of organic molecules present from a determination of the degree to which the polarized beam is rotated when it passes through the eluent.

12 Claims, 4 Drawing Figures

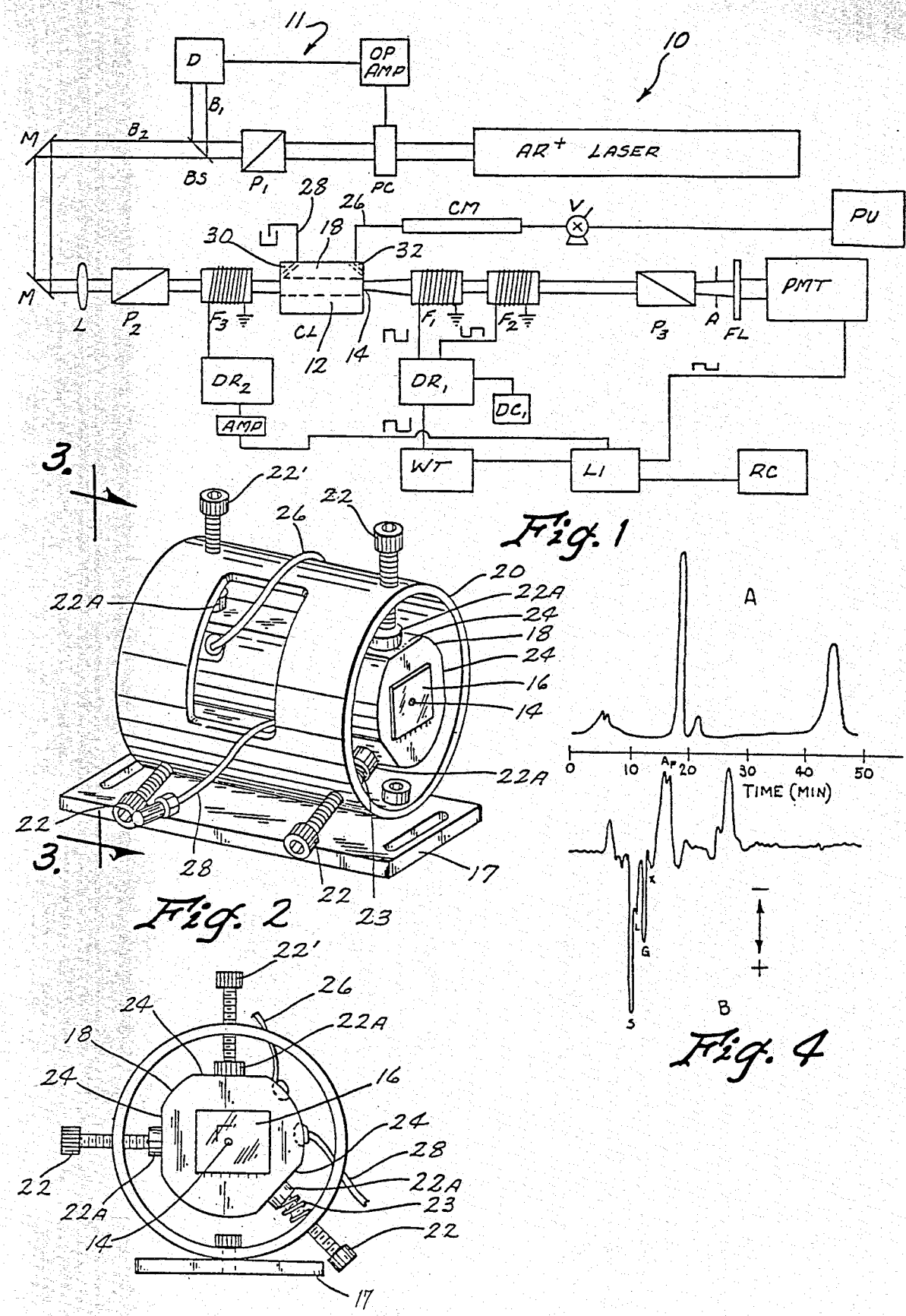

MICRO-POLARIMETER FOR HIGH PERFORMANCE LIQUID CHROMATOGRAPHY

GRANT REFERENCE

This invention was made in part under Department of Energy contract No. W-7405 ENG-82.

This is a continuation-in-part of application Ser. No. 286,026 filed July 22, 1981, now abandoned.

BACKGROUND OF THE INVENTION

The increased concern over the environment and the increased use of chemical information in clinical diagnosis has led to heightened interest in a practical device for trace organic analysis. Analysis of volatile organics is now nearly a routine matter due to the availability of capillary column gas chromatography, particularly when the same is interfaced to mass spectrometers. However, species of organic molecules which are not volatile enough for gas chromatography remain beyond the limits of prior detectors. High performance liquid chromatography (hereinafter HPLC), in practice, did not offer an alternative to analysis of the non-volatile organics. Prior HPLC systems either lacked a sufficient resolution during relatively high speed analysis or required hours to provide adequate data. The corresponding liquid chromatography-mass spectrometer interface also has many difficulties remaining.

Furthermore, the limitations of optical detectors for HPLC are many. Organic molecules lacking convenient absorption bands generally limited HPLC to analysis of unsaturated compounds. Even the far ultraviolet and Fourier Transform infrared detectors are constrained by the possible choice of eluents. Similarly, refractive index detectors generally lack sensitivity and selectivity, particularly when gradient elution is needed for proper separation of test samples. Chemical derivatization to overcome some difficulties, either before or after separation, could improve results, but again convenience and reliability are degraded.

Flame ionization and cation exchange resins have also been used for analysis, but this combination lacks sensitivity. Paper chromatography provides qualitative information in a reasonable time, but even semi-quantitative results are difficult to obtain at low concentration levels.

Since conformation is so specific a property for biological processes, many important clinical and environmental samples involve optically active molecules. Further, most eluents are not optically active. Accurate determination of the optical rotary powder of a sample can provide information regarding its isomeric purity and can provide quality control in pharmacological and food related industries. Thus, an HPLC detector based on optical activity would possess many advantages in the problematic areas of organic analysis. But, prior instrumental limitations have not allowed extension of this principle to micro and trace analysis. Attempts have been made to use optical activity to monitor column chromatography. Again, however, the extension to HPLC was not achieved due to the many technical difficulties associated with operating at the limit of detectability.

Accordingly, it is a principal object of the present invention to provide an apparatus which can analyze trace and microlevels of organic molecules which are not volatile enough for gas chromatography.

A further object of the present invention is to provide a micro-polarimeter for an HPLC which can provide micro and trace level analysis of optically active organic molecules in a relatively short period of time.

A still further object of the present invention is to provide a micro-polarimeter for an HPLC which is reliable and economical to use.

SUMMARY OF THE INVENTION

An argon laser beam is focused by a lens and polarized by a prism polarizer, and the polarized light is directed along the longitudinal axis of a flow cell. The flow cell has a narrow, central bore which communicates near each end with a conventional liquid chromatography pumping system. Human urine samples are introduced into the eluent (water) and the eluent is irradiated by the polarized beam.

Thin, microscope cover slips serve as cell windows covering the ends of the bore. A second prism polarizer is placed in front of the exit end of the bore and serves as an analyzer. The slips are mounted slightly off normal to the path of the laser beam with silicone sealant.

Matched air gap Faraday rotators are placed between the cell and the analyzer. The rotators produce a magnetic field which modulates the transmitted polarized beam so that the detection of minute rotations in the direction of polarization is enhanced.

After the beam passes through the analyzer, it is directed through an interference filter to screen out stray light and the light beam is converted into an electrical signal by a photo-multiplier. A lock-in amplifier set to the modulation frequency of the laser beam amplifies the output signal. The direction and degree to which the electric field of the initial polarized beam is rotated, is determined and recorded from the output signal. Comparison of the output data to calibration runs allows determination of the presence and concentration of sugars in the urine samples to a level of 0.10 micrograms.

BRIEF DESCRIPTION OF THE DRAWINGS

FIG. 1 is a schematic of the micro-polarimeter and associated circuitry.

FIG. 2 is a perspective view of the flow cell.

FIG. 3 is an end view of the flow cell along line 3—3 of FIG. 2.

FIG. 4 is a typical sample of the output of the micro-polarimeter and a comparison of the same to the output of an ultraviolet detector.

DESCRIPTION OF THE PREFERRED EMBODIMENT

An argon laser is interfaced with a system for high performance liquid chromatography (FIG. 1). Measurements of the optical activity of organic molecules suspended in the eluent of the chromatography system are determined by irradiating the eluent with a focused and polarized laser beam. The degree to which the electric field vector of the polarized laser beam is rotated is utilized to determine the concentration of particular organic molecules. The preferred embodiment is described by Yeung, et al. in *Detector Based On Optical Activity for High Performance Liquid Chromatographic Detection of Trace Organics*, 52 *Analytical Chemistry*, 1399, August 1980, and Kuo and Yeung, *Determination of Carbohydrates in Urine by HPLC and Optical Activity Detection, Journal of Chromatography*, Vol. 223, pp. 321, 1981.

Since it is found that a major source of noise in the ultimate output signal from the micro-polarimeter 10 of FIG. 1 is "shot noise" due to the incomplete extinguishing of the laser beam in the absence of a sample while the system for liquid chromatography is in operation, it is preferred that the laser light source first be passed through an intensity stabilization unit 11.

The unit consists of a Pockels cell (Lasermetrics Corporation Model 1058-FV, i.e., the specifications include a 116 mm aperture, a 600:1 extinction ratio, the $\frac{1}{4}$ wave retardation voltage is 2.1 Kv at 0.694 microns, an approximately 10 picofarad capacitance and a KDP crystal); an air spaced, open face, 10 mm aperture, Glan prism $P_1$ (Lambrecht Corporation, Model MGLS-DW-8); a beam splitter BS, (a 1 mm thick, grade 1 pyrex glass microscope slide disposed at a 45° angle, to the path of the laser beam); a balanced phototransistor/detector D and a high voltage operational amplifier (OP AMP in FIG. 1, Burleigh Instruments Model PZ-70).

With respect to the Pockels cell, a cell with a low voltage for $\frac{1}{4}$ wave retardation is preferable because it greatly simplifies the electronics. The extinction ratio could be as low as 10:1. For example, a Pockels cell with a 2.5 mm aperture, a 500:1 extinction ratio, a $\frac{1}{4}$ wave retardation voltage of 175 V. at 0.633 microns, a 125 picofarad capacitance and an ADP crystal (i.e., a Lasermetrics 3033) would be preferable to the Lasermetrics 1058-FV.

The laser beam is passed through the Pockels cell PC (which is initially unactivated) and is polarized by Glan Prism $P_1$. The polarized beam is split by beam splitter BS while a small percentage $B_1$ (approximately 6% in actual runs) of the beam is directed to photodetector D. Detector D compares $B_1$ with an adjustable reference level. If there is a difference between the reference level and $B_1$, an error signal (which is proportional to the degree of difference) is sent from detector D to the OP AMP. The error signal is amplified and used to activate the Pockels cell. Upon activation the Pockels cell will generate an electric field proportional to the input signal. As is well known, Pockels cell PC will alter the indices of refraction of birefringent crystals in the cell in proportion to the strength of the applied electric field. This in turn will alter the intensity of the laser beam in the direction of polarization of prism $P_1$. Thus, the intensity of the beam transmitted by prism $P_1$ will be corrected and stabilized.

The non-deflected portion of the laser beam (i.e., $B_2$), is directed to lens L by two mirrors M (aluminum coating on a glass flat, the flatness thereof being within at least $\frac{1}{4}$ of the laser's operating wave length). Lens L is a 1 m.f.l. crown glass lens, which focuses the laser beam within the flow cell and directs it along the longitudinal axis of flow cell CL. Lens L is also positioned such that its focal point will lie at the approximate center of flow cell CL. Flow cell CL is 10 cm. long and has a narrow bore 12 along its longitudinal axis through which the eluent flows. It is necessary to provide a narrow beam which will fit within the dimensions of the bore of the cell. The one meter focal length of lens L provides such a beam which is essentially collimated within the length of the flow cell.

Glan prisms $P_2$ and $P_3$ (Lambrecht Corporation Model MGT-25E8-45 which are air spaced with an approximate 10 mm. aperture) are placed between lens L and flow cell CL, and after flow cell CL, respectively. The prisms are placed in the path of the laser beam with prism $P_2$ serving as polarizer and prism $P_3$ as the analyzer. To prevent inter-cavity depolarization in lens L, the lens L must be placed before prism $P_2$.

It is important to isolate the system from vibration since misalignment of the analyzer $P_3$, flow cell CL and polarizer $P_2$ will result in significant noise in the output signal. Prisms $P_2$ and $P_3$ are mounted (open faced mount is preferred but closed is possible) in rotational stages (not shown), with a resolution of $10^{-3°}$. An open center rotational stage, adjustable (but not necessarily readable) to $10^{-3°}$ is used.

Further, the rotational stages, prisms $P_2$ and $P_3$, and flow cell CL must be isolated from vibrations which would cause rotational displacement of any of said three elements relative to any of the others on the order of $10^{-3°}$. Isolation of these elements on the order of $10^{-4°}$ or even $10^{-5°}$ is preferable. Isolation from such vibrations is generally possible by simply using a very rigid table, however, if needed, a vibration-isolated optical table can be used. Such a table would include a $4' \times 10' \times 8''$ table top, a 3/16'' ferromagnetic stainless steel top skin, a carbon steel bottom skin, a steel honeycomb core of 14 pounds/ft$^3$ density with a 0.4 sq. in. cell area, a flatness of $\pm 0.005''$ and three free standing pneumatic isolation mounts for vibration isolation and self-leveling. For further precautions, a breadboard system with a $4' \times 8' \times 2.3''$ breadboard can be used. The breadboard is similar to the optical table but it has an aluminum honeycomb core with a 5.2 lb/ft$^3$ density and no legs. The important parameters to control (i.e., limited to less than $10^{-30°}$) to insure sufficient vibration isolation are torsion and flex of the mounting system at the modulation frequency of the Faraday rotators (modulation frequency is discussed below).

Misalignment of the beam steering optics (i.e. the laser, mirrors, stabilization unit 11 and lens L) could also adversely affect the output of micropolarimeter 10. The steering optic system should have a beam pointing stability better than 0.5 milliradians. If the pointing stability is 0.5 milliradians or higher, significant noise will be added to the output thereby substantially affecting the operation of micropolarimeter 10.

Stray light entering the photomultiplier PMT (which is located after the analyzer and is a 56 DVP photomultiplier tube operated at 1600 V) will also substantially dilute the quality of the output signal. Stray light is reduced by keeping the prisms $P_2$ and $P_3$ about two meters apart and providing an aperture A (A is a 4 or 5 mm. hole in a metal sheet with a nonreflective, e.g., flat black paint, coating) between the analyzer $P_3$ and the photomultiplier PMT. A two meter distance is set between aperture A and the photomultiplier PMT. Further, an optical filter FL (i.e., a dielectric interference filter with a 30% transmission and a $10 \pm 2$ Å bandwidth) centered around the operating wave length of the laser (to within $+2$ Å) and placed between the aperture A and photomultiplier PMT is important to block stray light. Alternately, darkening the room may serve or assist the same basic function as the filter FL.

The dimensions of center bore 12 of flow cell CL are important. Micropolarimeter 10 is designed to measure very small degrees of rotation in the electric field of the incoming polarized light. Since the degree to which the electric field vector of the polarized light is rotated is directly proportional to the path length of the light within an optically active sample, a longer path length will mean a larger degree of rotation for a given sample, which in turn will make measurement easier.

However, if too large a volume is provided in the flow cell in order to obtain the long path length, it will be difficult to provide a system for chromatography which will permit the resolution of a single optically active specimen. A good rule of thumb is for the detector volume to be about one-fifth of the eluted volume which for normal HPLC means a maximum detector volume of about 200 microliters. That is, the column of the system for HPLC is designed to separate various optically active molecules and pass them through at different times. The degree of separation is limited, however, and it is thus desirable to look at only a small volume of the eluent at any given time. If the volume is too large, two different kinds of optically active molecules may pass through the flow cell at the same time, making it impossible to determine what portion of the rotation of the direction of polarization is due to one kind of molecule, and what portion is due to the other kind.

To accommodate these competing interests, the cell bore 12 should be long to maximize signal strength, yet narrow to the extent the focused laser beam is not reflected off the cell walls, is preferable. In the embodiment described an 80 microliter volume with a $1.016 \times 10^{-1}$ cm diameter and 10 centimeter length was used for bore 12. The flow cell CL includes an aluminum housing 18 for thermal stability.

For the proper operation of micropolarimeter 10, it is important to transmit only highly polarized light through the polarizer $P_2$, flow cell CL and analyzer $P_3$. That is, only light with the electric field vector in a selected plane should be transmitted. It will be difficult to obtain accurate data on changes in the direction of polarization of the light after it has passed through flow cell CL if light polarized in other directions is allowed to reach the analyzer $P_3$ and photomultiplier PMT. Therefore, maintenance of a high extinction ratio (i.e., the ratio of the magnitude of the transmitted electric field vector in the direction of polarization to the magnitudes of the electric field vectors of the transmitted light in all other directions) through the polarizer $P_2$, flow cell CL and analyzer $P_3$ is desirable.

The manufacurer's specifications for Glan prism $P_2$ and $P_3$ provide only a $10^6$ extinction ratio. However, by carefully selecting particular crystals and localized regions therein which are free from imperfections, extinction ratios between the combination of prisms $P_2$ and $P_3$ as high as $10^{10}$ can be readily achieved. The selection process involves adjusting the position of prisms $P_2$ and $P_3$ individually in separate, parallel planes which are perpendicular to the path of the laser beam (in the absence of a sample) until the minimum output provides a peak for light transmitted with analyzer $P_3$ oriented for extinction. By first screening prisms $P_2$ and $P_3$ for imperfections, and by particularly examining the half of polarizer $P_2$ away from the light source nd the half of analyzer $P_3$ towards the source (a "half" of a Glan prism $P_2$ and $P_3$ being the half volumes thereof depicted in FIG. 1 defined by the diagonal lines across $P_2$ and $P_3$) the selection process is greatly enhanced. This later precaution is helpful because these particular halves of prisms $P_2$ and $P_3$ are the major contributing parts of the polarizer $P_2$ and analyzer $P_3$ to the transmission of unwanted light.

The $10^{10}$ extinction ratio should be maintained as much as possible during the passage of the laser beam through flow cell CL. As seen in FIGS. 2 and 3, the ends 14 of bore 12 in housing 18 are covered by flat microscope cover slips 16 (1"×1"×0.010" pyrex, grade 1) which serve as cell windows. The cell windows introduce additional scattering centers and birefringence. It is importance to minimize these scattering centers. It was found by experiment that one out of ten standard commercial cover slips will have small regions of several square millimeters which will allow transmission of the polarized laser beam without materially affecting the operation of micropolarimeter 10 when extinction ratios of $10^{10}$ are employed. The location of said small regions in the cover slip 16 is accomplished by a similar process of moving the slips in separate, parallel planes which are perpendicular to the laser beam as described with regard to selection of prisms $P_2$ and $P_3$.

Further, to keep the cell windows strain free so as not to introduce further scattering problems, a silicone sealant cement (e.g., Dow Corning Silicone Rubber Sealant) is a preferred way to maintain slips 16 over ends 14.

Alignment of the flow cell CL is also important. Reflections off the cell walls and off normal reflections at the cell windows were found by experimentation to be a major contribution to noise.

If the laser beam is not directed along the axis of the flow cell CL, the beam can be scattered and reflected off the flow cell CL walls, which will cause depolarization of the beam. Careful positioning of the flow cell CL is required and the use of dual X-Y positioners (as further described below) is highly desirable.

As shown in FIGS. 2 and 3, cell CL has a base 17 and housing 18 which is surrounded in spaced concentric relation by an annular casing 20. Casing 20 has six screws 22 (only five are shown) which pass through casing 20 adjacent to the casing's ends and serve as X-Y positioners. Two screws are set 90° apart and the third 135° from each of the first two, around the circumference at two locations. Housing 18 has three flattened portions 24 which provide even surfaces for screws 22 and sliding flats 22a to press against, and springs 23 on the third screws to put constant tension on the 90° (orthogonal) adjusting screws to align the cell. Tubes 26 and 28 pass through housing 18 and provide inlet and outlets to the remainder of the HPLC system and are connected to bore 12 by way of passageways 30 and 32 in the housing 18 (FIG. 1). Passageways 30 and 32 are 0.89 mm in diameter and placed at 60° with respect to bore 12.

It is necessary that the eluent chosen does not absorb substantially in the range of the wave length of the light source. Otherwise, the eluent will be heated and thermal lensing i.e., alteration of the index of refraction of the eluent, will occur at the site of the absorption, which in turn will cause refraction of the laser beam. Further, bubbles or impurities in the eluent will cause intra-cavity depolarization at the sites thereof. It is found that bubbles can be avoided by keeping the cell walls wet and care should be used in selecting and degassing pure eluents.

A further important feature to micro-polarimeter 10 is the use of air gap Faraday rotators to modulate the polarization of the output beam, which allows smaller output signals to be distinguished from noise. Modulation of the beam marks the electric field of the polarized beam with a frequency. Lock-in amplifier L1 receives the output from the photomultiplier PMT and is set to amplify only the signal of the modulated frequency. Lock-in amplifier L1 is a P.A.R. HR-8 with a 100 k ohm input impedance to class "A" preamplifiers, and includes a 12 db/octave, tunable input filter with the sensitivity dependent on the gain of photomultiplier PMT.

It is essential that the modulator be placed between the polarizer $P_2$ and analyzer $P_3$. Placement of the modulating mechanism after the flow cell CL was found by experimentation to assist in beam alignment. Further, since birefringence in the flow cell windows 16 depends on the direction of polarization, decoupling of the applied modulation from the input beam (again by placing the modulator after the cell) provides a better signal to noise ratio.

Two matched air gap Faraday rotators $F_1$ and $F_2$ (FIG. 1) are utilized to provide the modulation. Faraday rotators $F_1$ and $F_2$ are based on air as the active medium and are constructed by winding 8000 turns of #30 gauge magnet wire along 10 cm of 4.8 mm o.d., thin-wall, non-ferromagnetic stainless steel tubing. A wave generator WT is connected to a switching amplifier/driver $DR_1$, to drive Faraday rotators $F_1$ and $F_2$ during alternate half cycles of a square wave input. Wave generator WT is a frequency tunable signal generator which should preferably generate a 1 V square wave from 10 to 2000 Hz with a synchronized square wave synch-signal. The switching amplifier driver DR, should be triggered by a 5 V square wave and be capable of operating continuously at approximately 2 amperes (with 0.5 ampere being the minimum operating level). Driver DR utilizes a direct current, variable 0–25 V power supply $DC_1$.

Faraday rotators F1 and F2 provide about 1,000 gauss per ampere of current which produces approximately $4 \times 10^{-3°}$ of rotation per ampere. Faraday rotators F1 and F2 utilize only air as a medium since because the use of quartz or a liquid might add additional scattering centers or cause strain induced birefringence. For small angles of rotation of modulation (which is always the case), the transmitted beam intensity I is given by $4I_o{}^\alpha\delta$ where $I_o$ is the incoming intensity, $\delta$ equals the angle of rotation due to the sample, and $\alpha$ is the modulation angle. Thus, a large modulation angle is desirable (provided the stability of the modulation is better than $\delta$). The modulation frequency is otherwise arbitrary, but should be selected to coincide with a relatively noise free region in the operating environment.

The output of lock-in amplifier LI is passed through a conventional recorder RC. Recorder RC should preferably be capable of accepting a DC analog output from the lock-in amplifier with a time constant of less than 10 Hz ($\pm 10$ VDC for the HR-8). The output resolution of the trace should preferably be less than 0.3%.

Output data for a system adapted to analyze monosaccharides is shown in FIG. 4. Upper Section A of FIG. 4 is the output from an ultraviolet detector (not shown) for the analysis of an eluent containing human urine (displayed as a function of time). The ultraviolet detector is a conventional (e.g., a Spectra Physics Chromatronix, Santa Clara, Calif., Model 210), absorbance detector and is used at 254 nm in series with the flow cell CL (i.e., between flow cell CL and column CM). The area under the peaks in portion A of FIG. 4 represent concentration of particular monosaccharides. Portion B of FIG. 4 is the same sample as depicted in Portion A, but the data is of the output from micropolarimeter 10. The minus and plus signs indicate the direction of rotation with the negative direction being levorotatory and the plus direction being dextrorotatory. The areas under the respective peaks again represent concentrations of the various sugars. S is sucrose, L is lactose, G is glucose, X is xylose, A is arabinose and F is fructose.

For fine alignment, a third air gap Faraday rotator F3 (FIG. 1) may be employed as a compensator. Faraday rotator F3 is similar to rotators F1 and F2 but requires heavier wire and construction to carry approximately 5 to 10 amperes. One possible configuration for the compensator is as a feedback mechanism which receives input from LI, by way of a driver $DR_2$ and amplifier AMP. Driver $DR_2$ differs from $DR_1$ in that $DR_2$ is a DC driver.

If lock-in amplifier LI is adjusted for zero signal at the null or 0° rotation point, the output from lock-in amplifier LI to the compensator driver $DR_2$ is zero and Faraday Rotator F3 is not activated. If lock-in amplifier LI detects any signal other than a null signal, a correcting signal is sent to the Faraday rotator F3 by way of driver $DR_2$ to alter the medium therein (again air) and counter rotate the polarization of the light. This correction continues until the lock-in amplifier LI again receives a null signal. The recorded output for this configuration is the signal sent to Faraday Rotator F3 which is directly proportional to the amount of rotation induced by the sample.

The column CM used to obtain the output in FIG. 4 is a Bio-rad Laboratories Corporation, Model HPX-87 heavy metal cation exchange column (i.e., an 8% cross-linked, 9 micron diameter particles for carbohydrate analysis, 250 mm. long × 4.6 mm. I.D. column). The operating conditions were as recommended by the manufacturer, i.e., pump PU was operated at a flow rate of 0.64 milliliters per minute. Water was used as the eluent which was maintained at 85° C. All injections were through a 100 microliter loop at a conventional injection valve V. Pressure fluctuations caused by the pump were reduced by a commercial pulse dampener. Pressure fluctuations were further reduced as a result of having said conventional ultraviolet absorbance detector in series, and before the optical activity detector. Since the flow cell CL was essentially at room temperature, the eluent was cooled to some extent from 85° C. so that turbulence would not exist in the flow cell CL. It was found that having the ultraviolet detector in series was sufficient for cooling (note that an extra length of tubing would supply the same cooling effect). The laser was a Control Laser Corp. Model 554 argon ion laser operated at 488 nm and 500 mW.

It is apparent from FIG. 4 that the sensitivity of the present invention far exceeds that of the ultraviolet detector displayed in A. Utilizing the above precautions, an extinction ratio of $10^{10}$ is regularly achieved. In addition, for the data displayed in FIG. 4, a detection limit of 0.10 micrograms was possible.

The limit of detection can be reduced to approximately 0.02 micrograms if the following factors are reduced: (1) residual depolarized light through the crossed polarizers, (2) residual pumping noise in the eluent which causes the windows to distort, (3) the remaining $\pm 1\%$ noise in the laser, and (4) dust particles in the optical path.

Variations in the above device are possible, which will still allow trace and microanalysis of optically active samples by the use of a micro-polarimeter for an HPLC. However, because the limit of sensitivity is being approached, variations to the preferred embodiment must be carefully made. Since noise is proportional to the square root of the number of photons in a signal, the ratio of signal to noise will be increased with increased photons statistics. This implies that the use of a laser will enhance the signal to noise ratio.

Similarly, various lasers could be utilized. For example, a He-Ne (helium-neon) laser has been used. However, the intensity of a He-Ne laser is more difficult to stabilize. A He-Ne laser with a power of approximately 10 to 50 milliwatts could be used without sacrificing significant performance from the argon laser, and at less cost. Also, when lower power lasers are used, the system takes less time to warm up. This is because heating causes changes in birefringence in the polarizing crystals as well as the cell windows. Thus, lower power lasers are desirable up to the limit discussed above due to photon statistics (i.e., the signal to noise ratio becomes smaller as power is reduced). Further, if the power is too low, stray light becomes a problem (e.g. stray light was found to be a problem for a 2 mW He-Ne laser). However, further experimentation with a 2 mW He-Ne laser did reveal that detectability on a one microgram level was possible even at such low power. This indicated that contrary to a prior estimate, photon statistics was not the major limiting factor in the case of the argon ion laser.

Data for the present embodiment is displayed concerning only carbohydrates; however, the system could be adapted to be utilized with virtually any optically active organic molecule. In particular, if non-carbohydrates were of interest, one must adjust the wave length of the light source to insure that the sample would not absorb the light. Additionally, the solvent utilized in the column would have to be optimized for non-absorbance. Further care must be taken to avoid abrupt changes in concentration through the flow cell which would distort the beam.

From the above description, it is seen that the present invention accomplishes at least all of its stated objectives.

What is claimed is:

1. An apparatus for determining trace and micro levels of selected species of optically active molecules in a non-optically active eluent which is cycled through a calibrated system for high performance liquid chromatography, comprising:

a flow cell with flat ends through which the eluent is cycled along a central bore, the bore having an input opening in one end of the cell and an output opening in the other end, and wherein the volume of the flow path between the openings is sufficiently small to allow substantially only one species of the selected molecules to be in the volume at any time;

transparent, flat, cell windows which are mounted substantially strain free over the openings, and which allow light to pass without substantial scattering, reflection or refraction;

a laser adapted to irradiate said input opening along the longitudinal axis of the central bore and to output at least two milliwatts when energized, and wherein the operating wave length of the laser will not be substantially absorbed by the molecules or the eluent so that thermal lensing is prevented;

a polarizer positioned between the laser and flow cell so that a beam from the laser will be polarized before entering the input opening;

a lens focusing the laser beam positioned between the laser and the polarizer so that the laser beam will be polarized and collimated while passing through the flow cell without substantially being reflected off the flow cell walls;

means for aligning said laser and lens whereby said laser and said lens in combination will have a beam pointing stability of at least 0.5 milliradians;

an analyzer positioned after the exit opening so that the polarization of the laser beam after the beam has passed through the flow cell can be determined, said polarizer and analyzer being selected so that an extinction ratio of at least $10^{10}$ is achieved between the combination thereof;

means for isolating said polarizer, analyzer and flow cell from vibrations which would effect their relative angular position on the order of $10^{-3°}$;

means for modulating the laser beam at a frequency in a substantially noise free region of the environment, and which is positioned between the polarizer and the analyzer in the path of the laser beam; and means for filtering light, adapted to pass only light centered around the operating wave length of the laser beam and positioned in the path of the laser beam after the beam exits the analyzer so that the filtered, modulated beam can be converted to an electrical signal containing information on the direction and degree to which the polarized laser beam was rotated when it passed through the flow cell.

2. The device of claim 1 wherein said modulating means includes a Faraday rotator having air as a medium and a means for driving said rotator in response to a periodic electric signal.

3. The device of claim 1 further comprising an aperture positioned between the analyzer and the filter to further prevent stray light from entering the conversion means.

4. The device of claim 1 wherein:

said transparent cell windows are microscope cover slips which are mounted slightly off normal on the flow cell with silicone sealant, said laser is an argon ion laser operated at 0.5 W and 488 nm, and the distance between the polarizer and the analyzer is two meters.

5. The device of claim 1 further including a means for stabilizing the intensity of a beam from the laser and positioned between the laser and the polarizer in the path of the laser beam.

6. The device of claim 1 wherein the intensity stabilization means comprises:

a Pockels cell;

a Glan prism;

a beam splitter, wherein the Pockels cell, Glan prism and beam splitter are in the path of the laser beam between the lens and the laser, and the Glan prism is between the Pockels cell and beam splitter;

a photodetector adapted to receive the portion of the laser beam which is split from the initial path of the laser beam by the beam splitter and which is adapted to output an electrical signal if the portion of the beam thus split differs in intensity from a predetermined level; and an operational amplifier adapted to receive the electrical signal from the photodetector and to adjust the Pockels cell in response thereto so that the intensity of the laser beam is stabilized.

7. The device of claim 1 further including a means for converting the modulated laser beam to an electric signal.

8. The device of claim 7 wherein said conversion means is a photomultiplier.

9. The device of claim 8 further comprising:
means for detecting the frequency of the converted light signal;
means for generating a first signal in response to the detection of electrical signals with a frequency equal to the modulation frequency;
means for generating a second signal in response to the detection of the amplitude and phase of the first signal at the modulation frequency; and
means for adjusting the modulation of the modulated beam in response to said second signal, and until said second signal is substantially zero.

10. The device of claim 1 wherein said adjustment means is a compensating Faraday rotator with air as a medium which is positioned between the polarizer and the analyzer in the path of the laser beam.

11. An apparatus for determining trace and micro levels of selected species of optically active molecules in a non-optically active eluent which is cycled through a calibrated system for high performance liquid chromatography, comprising:
a flow cell with flat ends through which the eluent is cycled along a central bore, the bore having an input opening in one end of the cell and an output opening in the other end, and wherein the volume of the flow path between the openings is sufficiently small to allow substantially only one species of the selected molecules to be in the volume at any time;
transparent, flat, cell windows which are mounted substantially strain free over the openings, and which allow light to pass without substantial scattering, reflection or refraction;
a laser adapted to irradiate said input opening along the longitudinal axis of the central bore and to output at least two milliwatts when energized, and wherein the operating wave length of the laser will not be substantially absorbed by the molecules or the eluent so that thermal lensing is prevented;
a polarizer positioned between the laser and flow cell so that a beam from the laser will be polarized before entering the input opening;
a lens for focusing the laser beam positioned between the laser and the polarizer so that the laser beam will be polarized and collimated while passing through the flow cell without substantially being reflected off the flow cell walls;
means for aligning said laser and lens whereby said laser and said lens in combination will have a beam pointing stability of at least 0.5 milliradians;
an analyzer positioned after the exit opening so that the polarization of the laser beam after the beam has passed through the flow cell can be determined, said polarizer and analyzer being selected so that an extinction ratio of at least $10^{10}$ is achieved between the combination thereof;
means for isolating said polarizer, analyzer and flow cell from vibrations which would effect their relative angular position on the order of $10^{-3°}$;
means for modulating the laser beam at a frequency in a substantially noise free region of the environment, and which is positioned between the polarizer and the analyzer in the path of the laser beam; and
means for filtering light, adapted to pass only light centered around the operating wave length of the laser beam and positioned in the path of the laser beam after the beam exists the analyzer so that the filtered, modulated beam can be converted to an electrical signal containing information on the direction and degree to which the polarized laser beam was rotated when it passed through the flow cell;
means for aligning said flow cell whereby reflections within said cell are substantially eliminated.

12. The apparatus of claim 11 wherein said means for aligning said flow cell includes a plurality of set screws adapted to engage said cell for adjustable positioning thereof.

* * * * *